US011472759B2

(12) United States Patent
Deeley et al.

(10) Patent No.: US 11,472,759 B2
(45) Date of Patent: Oct. 18, 2022

(54) ETHERIFICATION PROCESS

(71) Applicant: BP P.L.C., London (GB)

(72) Inventors: Jon Deeley, London (GB); Gareth Armitage, London (GB)

(73) Assignee: BP P.L.C., London (GB)

( * ) Notice: Subject to any disclaimer, the term of this patent is extended or adjusted under 35 U.S.C. 154(b) by 177 days.

(21) Appl. No.: 16/757,414

(22) PCT Filed: Oct. 19, 2018

(86) PCT No.: PCT/EP2018/078801
§ 371 (c)(1),
(2) Date: Apr. 19, 2020

(87) PCT Pub. No.: WO2019/077146
PCT Pub. Date: Apr. 25, 2019

(65) Prior Publication Data
US 2021/0363084 A1    Nov. 25, 2021

(30) Foreign Application Priority Data
Oct. 19, 2017 (GB) .................................... 1717211

(51) Int. Cl.
| C07C 41/06 | (2006.01) |
| C07C 41/20 | (2006.01) |
| C07C 41/28 | (2006.01) |
| C07C 41/56 | (2006.01) |
| C07C 43/04 | (2006.01) |
| C07C 43/303 | (2006.01) |
| C10M 105/18 | (2006.01) |

(52) U.S. Cl.
CPC .............. *C07C 41/06* (2013.01); *C07C 41/20* (2013.01); *C07C 41/28* (2013.01); *C07C 41/56* (2013.01); *C07C 43/04* (2013.01); *C07C 43/303* (2013.01); *C10M 105/18* (2013.01); *C07C 2523/44* (2013.01)

(58) Field of Classification Search
None
See application file for complete search history.

(56) References Cited

U.S. PATENT DOCUMENTS

| 3,102,150 A | 8/1963 | Hunter et al. |
| 4,088,700 A | 5/1978 | Watts, Jr. |
| 4,479,017 A | 10/1984 | Ayusawa et al. |
| 5,523,491 A | 6/1996 | Egawa et al. |
| 5,589,597 A | 12/1996 | Egawa et al. |
| 6,087,539 A | 7/2000 | Yamasaki et al. |
| 6,313,322 B1 | 11/2001 | Hieber et al. |
| 7,622,431 B2 | 11/2009 | Muir |
| 2005/0198894 A1 | 9/2005 | Migdal et al. |
| 2006/0090393 A1 | 5/2006 | Rowland et al. |
| 2013/0109604 A1 | 5/2013 | Patil et al. |

FOREIGN PATENT DOCUMENTS

| EP | 1533362 A1 | 11/2004 |
| GB | 1581412 A | 12/1980 |
| WO | 95/01949 A1 | 1/1995 |
| WO | 1999/021902 A1 | 5/1999 |
| WO | 2003/099890 A3 | 12/2003 |
| WO | 2004/046073 A1 | 6/2004 |
| WO | 2006/099250 A1 | 9/2006 |
| WO | 2014/096096 A1 | 6/2014 |

OTHER PUBLICATIONS

Gembus, V. et al. "Efficient Access to (All-rac)-α-Tocopherol Acetate by a Crombie Chromene Synthesis" Bull. Chem. Soc. Jpn. vol. 82, No. 7, 843-854 (2009) (Year: 2009).*
Rosini, G. et al. "Acid promoted CIDT for the deracemization of dihydrocinnamic aldehydes with Betti's base" Royal Society of Chemistry, Supporting information, 2010; pp. 1-7 (Year: 2010).*
International Search Report for PCT/EP2018/078801, 3 pages, dated Jan. 18, 2019.
International Search Report for PCT/E{2018/078802, 4 pages, dated Jan. 28, 2019.
Bakos et al., "Auto-Tandem Catalysis with Frustrated Lewis Pairs for Reductive Etherification of Aldehydes and Ketones" Angew. Chem. Int. Ed. 56: 5217-5221 (2017).
Smith et al., "Role of Acetal Formation in Metal Catalyzed Hydrogenation and Exchange of Cinnamaldehyde" Catalysis in Organic Synthesis, p. 33-65 (1977).
Eliel et al., "Reduction of Acetals to Ethers by Means of Lithium Aluminum Hydride-Aluminum Chloride" J. Org. Chem. 23: 1088 (1958).
Ohta et al., "Reductive cleavage of the C—O bond of acetals and orthoesters: reduction by silane in the presence of a Rh-PPh3 complex" Chem. Commun. 1192-1193 (2003).
Tsunoda et al., "Reaction of acetals and trialkylsilanes catalyzed by trimethylsilyl trifluoromethanesulfonate. A simple method for conversion of acetals to ethers" Tetrahedron Lett. 48: 4679-4680 (1979).
Post, "The Reaction of Certain Orthoesters with Aldehydes" Orthoesters and Aldehydes, 244-249 (1939).
Kotke et al., "Acid-free, organocatalytic acetalization" Tetrahedron, 62:434-439 (2006).
McElvain et al., "Ketene Acetals. XXIII. Dealcoholation of Orthoesters with Aluminum t-Butoxide" J. Am. Chem. Soc. 73: 1400-1402 (1951).
Claus et al. "A New Method of Conversion of Nitriles to Aldehydes 1" J. Am. Chem. Soc. 73(10): 5005-5006 (1951).

(Continued)

*Primary Examiner* — Medhanit W Bahta
(74) *Attorney, Agent, or Firm* — McDonnell, Boehnen, Hulbert & Berghoff LLP

(57) ABSTRACT

The present invention relates to a process for preparing ethers, particularly unsymmetrical ethers, and preferably ethers suitable for use as base stocks for lubricant compositions. In particular, the process involves the reaction of an α,β-unsaturated aldehyde with a trihydrocarbyl orthoester to form an α,β-unsaturated acetal and conversion of the α,β-unsaturated acetal to an ether through hydrogenation and hydrogenolysis.

20 Claims, No Drawings

(56) References Cited

OTHER PUBLICATIONS

Staudinger et al., "Ketene: Uber Ketenacetale" Helvetica Chimica Acti 5(5): 645-655 (1922).
Sigmund et al., "Uber die katalytische Spaltung von Orthoestern an Aluminumoxyd" Monatshefte Fur Chemie 58(1): 280-288 (1931).
Search Report for GB1717211.5, 2 pages, dated Aug. 1, 2018.
Search Report for GB 1717210.7, 2 pages, dated Aug. 1, 2018.
Bhattacharjee et al., "Hydrogenolysis of carbohydrate acetals, ketals, and cyclic orthoesters with lithium aluminum hydride-aluminum trichloride" Canadian J. Chem. 47(7):1195-1206 (1969).

* cited by examiner

ETHERIFICATION PROCESS

This application is a national stage application under 35 U.S.C. § 371 of International Application No. PCT/EP2018/078801, filed Oct. 19, 2018, which claims priority to Great Britain Application No. GB 1717211.5, filed Oct. 19, 2017, the disclosures of which are explicitly incorporated by reference herein.

The present invention relates to a process for preparing ethers, particularly unsymmetrical ethers, and preferably ethers suitable for use as base stocks for lubricant compositions. In particular, the process involves the reaction of an α,β-unsaturated aldehyde with a trihydrocarbyl orthoester to form an α,β-unsaturated acetal and conversion of the α,β-unsaturated acetal to an ether through hydrogenation and hydrogenolysis.

BACKGROUND

Ether compounds are an important category of compounds which have found application in a variety of industries as functional additives (for instance, cosmetic, fuel or lubricant additives), solvents, diluents and as important precursors for other industrial and/or commercially desirable compounds.

Known processes for preparing ethers on an industrial scale include the reaction of an alcohol with an alkyl group having a suitable leaving group, such as a halogen (for example bromine, chlorine or iodine) or a sulfonate ester (for example mesylate or tosylate), in the presence of a base (for example potassium hydroxide or potassium tert-butoxide) and a catalyst (for example Starks' catalyst: N-Methyl-N,N,N-trioctyloctan-1-ammonium chloride). However, such processes have the disadvantage of generating corrosive halogenated or sulfonate ester intermediates.

An alternative approach to etherification which avoids the formation of these undesirable intermediates is the reaction of an alcohol with an alkene. A well-known example of such an etherification relates to the preparation of methyl or ethyl tert-butyl ether (MTBE or ETBE), which are well known fuel additives. This same approach has also been utilized more recently in the preparation of ether compounds for use in improving one or more of solubility and dispersancy of lubricating compositions, as illustrated in US 2013/0109604 (Example 3 thereof).

Another approach to the formation of ethers which avoids the formation of corrosive by-products is through conversion of acetals to the corresponding ether by hydrogenolysis. Typically, this involves subjecting the acetal compound to hydrogen under conditions of elevated temperature and pressure in the presence of a suitable hydrogenation catalyst.

U.S. Pat. No. 5,523,491 describes the conversion of an acetal or ketal compound to the ether by means of hydrogenation in the presence of solid acidic catalyst having hydrogenating ability or a solid acid catalyst in combination with a hydrogenation catalyst. The process of the disclosure is said to be particularly suitable for forming polyvinyl ether compounds suitable for use in a lubricating oil for compression-type refrigerators. This document provides no indication of how the acetal/ketal starting materials may be formed.

U.S. Pat. No. 4,479,017 describes a catalytic hydrogenolysis of an acetal compound of formula (2) with a palladium catalyst on a carbon carrier to produce an ether compound. The acetal compound of formula (2) is said to be suitably derived from the standard reaction of an alcohol and a carbonyl compound (column 2, lines 38 to 47).

U.S. Pat. No. 6,087,539 describes the formation of a vinyl ether polymer compound of formula (II) or (III) from the reaction of a vinyl ether polymer of formula (I) having a terminal acetal group with hydrogen in the presence of a solid catalyst comprising nickel and an oxide of silicon, aluminium, magnesium, titanium, zirconium and combinations thereof. The starting material is said to be preparable from polymerization of an alkyl vinyl ether in the presence of an acetal compound and other conventional methods.

WO 95/01949 describes the conversion of acetals to ethers, in particular 3-alkoxypropiaonaldehyde dialkyl acetal to the corresponding 1,3-dialkoxypropane, in the presence of a supported hydrogenation catalyst comprising at least one catalytic metal selected from Pd, Ni, Co, Pt, Rh and Ru, and a supported material selected from silica, alumina silica-alumina, alumino-silicates and carbon.

Alternative methods for converting an acetal to the corresponding ether includes reduction with lithium aluminium hydride-aluminium chloride, as reported for instance in Eliel et al., J. Org. Chem., vol. 23, 1958, page 1088. Other methods of forming ethers from acetals include reductive cleavage of the C—O bond of the acetal with silane, as described in Chem. Commun., 2003, 1192-1193, and in Tetrahedron Letters, vol. 20, Issue 48, 1979, pages 4679-4680.

Where details of how the acetal compound employed in the above disclosures is itself prepared are provided, conventional methods are said to be relied upon, such as the reaction of an alcohol and a suitable aldehyde. This reaction typically requires the presence of an acidic catalyst.

An alternative method for forming an acetal compound is by reaction of an aldehyde and an orthoester. Post H. W., "*The Reaction of Certain Orthoesters with Aldehydes*", Orthoesters and aldehydes, 1939, pages 244 to 249, describes the reaction of an alkyl orthoformate with acetaldehyde, catalyzed by concentrated sulfuric acid, to produce the corresponding acetal. More recently, Schreiner et al., "*Acid free, organocatalytic acetalization*", Tetrahedron, 63, 2006, pages 434 to 439, reviews the use of different catalysts for acetalization reactions and proposes an alternative non-acidic catalyst in the form of an electron deficient thiourea derivative which may be used for acetalization of an aldehyde with an alkyl orthoester.

α,β-unsaturated aldehydes incorporating substitution at the α-position or β-position have been found by the inventors to represent particularly desirable starting materials for the formation of ether compounds that are especially suited for use in lubricating compositions. Lubricating compositions generally comprise a base oil of lubricating viscosity together with one or more additives to deliver properties including for example, reduced friction and wear, improved viscosity index, improved dispersancy, detergency, and resistance to oxidation and corrosion. A lubricant base oil may comprise one or more lubricating base stocks.

Lubricant base stocks used in automotive engine lubricants are generally obtained from petrochemical sources, for example they may be obtained as the higher boiling fractions isolated during the refining of crude oil or as the products of chemical reactions of feedstocks from petrochemical sources. Lubricant base stocks can also be made from Fischer-Tropsch wax.

Lubricant base stocks may be classified as Group I, II, III, IV and V base stocks according to API standard 1509, "ENGINE OIL LICENSING AND CERTIFICATION SYSTEM", 17th Edition, Annex E (October 2013 with Errata March 2015), as set out in Table 1.

TABLE 1

| Group | Saturated hydrocarbon content (% by weight) ASTM D2007 | | Sulphur content (% by weight) ASTM D2622, D4294, D4927, D3120 or D1552 | | Viscosity Index ASTM D2270 |
|---|---|---|---|---|---|
| I | <90 | and/or | >0.03 | and | ≥80 and <120 |
| II | ≥90 | and | ≤0.03 | and | ≥80 and <120 |
| III | ≥90 | and | ≤0.03 | and | ≥120 |
| IV | | | Polyalphaolefins | | |
| V | | | all base stocks not in Groups I, II, III or IV | | |

Group I base stocks are typically manufactured by known processes including, for example, solvent extraction and solvent dewaxing, or solvent extraction and catalytic dewaxing. Group II and Group III base stocks are typically manufactured by known processes including, for example, catalytic hydrogenation and/or catalytic hydrocracking, and catalytic hydroisomerisation. Group IV base stocks include for example, hydrogenated oligomers of alpha olefins.

A combination of properties is desirable in a base stock. In some instances, for example in passenger car engine oils, it may be desirable for a base stock to confer a low viscosity profile on the lubricant composition, since this leads to improved fuel economy. In particular, it is desirable for base stocks to have a low kinematic viscosity as well as good low-temperature viscosity characteristics, for example a low pour point or low viscosity as measured using a mini-rotary viscometer (MRV). However, the general trend is for an improvement in the viscosity profile (i.e. a reduction in viscosity parameters) of a base oil to be accompanied by an undesirable increase in volatility. Desirable base stocks are therefore those having low volatility for a given viscosity profile, but which are also suitable for use, for example, in a lubricating composition for an internal combustion engine.

Ether base stocks derived from α,β-unsaturated aldehydes have been found by the inventors to be particularly useful in conferring desirable properties on lubricating compositions, particularly where the base stocks are based on unsymmetrical ethers. α,β-unsaturated aldehydes may also be conveniently obtained from aldol condensation reactions. However, problems associated with using α,β-unsaturated aldehydes as starting materials include ensuring selectivity towards unsymmetrical ether products and the necessity for removing the double bond as part of forming an ether derivative, for instance by an additional hydrogenation step, or other suitable conversion step. It would be desirable to be able to overcome these problems without complicating conventional process and reactor design used in connection with etherification reactions and without increasing the number of steps in the overall synthesis.

It has been found by the inventors that the manner and order of the steps in which an α,β-unsaturated aldehyde is converted to a desirable ether is critically important for being able to obtain the desired ether selectively and in good yield, whilst reducing the overall number of steps to improve process economy. The present invention is based on the surprising discovery of an expedient process for the production of desirable ethers from α,β-unsaturated aldehydes.

SUMMARY

Accordingly, in a first aspect, an etherification process is provided, said process comprising the steps of:
i) contacting an α,β-unsaturated aldehyde with a trihydrocarbyl orthoester to form an α,β-unsaturated acetal; and
ii) subjecting the α,β-unsaturated acetal obtained from step i) to hydrogenation and hydrogenolysis to hydrogenate at the α- and β-positions of the α,β-unsaturated acetal and to convert the acetal group to an ether.

In a particularly preferred embodiment, the α,β-unsaturated aldehyde is of formula (I):

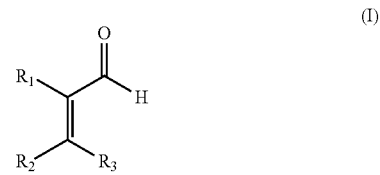

(I)

where $R_1$ and $R_3$ are independently selected from H and aliphatic hydrocarbyl; and $R_2$ is aliphatic hydrocarbyl, preferably wherein $R_1$ and $R_2$ are aliphatic hydrocarbyl and $R_3$ is H. In another particularly preferred embodiment, wherein the trihydrocarbyl orthoester is of formula (II):

(II)

where $R_4$ is selected from $C_4$-$C_{40}$ alkyl, $C_3$-$C_{40}$ cycloalkyl and $C_4$-$C_{40}$ cycloalkyl-substituted-alkyl and $R_5$ is selected from H and $C_1$-$C_{12}$ alkyl, $C_3$-$C_{12}$ cycloalkyl and $C_4$-$C_{12}$ cycloalkyl-substituted-alkyl.

Also provided are processes which, following preparation of the ether compound, include formulation of a lubricating composition comprising the ether compound and use of the resulting lubricant composition for lubricating a surface, such as a surface of an internal combustion engine associated with an automotive vehicle.

DETAILED DESCRIPTION

A process is provided for preparing an ether, said process comprising the steps of:
i) contacting an α,β-unsaturated aldehyde with a trihydrocarbyl orthoester to form an α,β-unsaturated acetal; and
ii) subjecting the α,β-unsaturated acetal obtained from step i) to hydrogenation and hydrogenolysis to hydrogenate at the α- and β-positions of the α,β-unsaturated acetal and to convert the acetal group to an ether.

For the purposes of the present invention, the following terms as used herein shall, unless otherwise indicated, be understood to have the following meanings: The term "hydrocarbyl" as used herein, including as used in connection with the trihydrocarbyl orthoester reactant employed in the process of the invention, refers to an aliphatic group comprising hydrogen and carbon atoms, where one or more carbon atoms may optionally be replaced with —O—, which may be saturated or unsaturated, preferably saturated, and contains up to 40 carbon atoms. Examples of hydrocarbyl groups include hydrocarbyl groups containing from 4 to 28 carbon atoms, such as from 6 to 26 carbon atoms or from 8 to 24 carbon atoms. Where one or more of the carbon atoms is replaced with —O—, from 2% to 35% of the carbon atoms are preferably replaced with —O—, or from 5% to 25%. In other examples, the hydrocarbyl group has 1 to 3 carbon atoms replaced with —O—, for example 2 carbon atoms replaced with —O—. In other examples, none of the carbon atoms are replaced with —O—. The hydrocarbyl group may be aromatic or aliphatic, or comprise both aromatic and aliphatic portions. Preferably, the hydrocarbyl group is aliphatic or at least comprises an aliphatic portion.

Examples of hydrocarbyl groups include acyclic groups, non-aromatic cyclic groups, aromatic groups and groups comprising both an acyclic portion and a non-aromatic cyclic/aromatic portion. The hydrocarbyl group may be a straight-chained or branched-chained group. The hydrocarbyl group includes monovalent groups and polyvalent groups as specified. Examples of monovalent hydrocarbyl groups include alkyl, alkenyl, alkynyl, carbocyclyl (e.g. cycloalkyl, cycloalkenyl or aryl) and aralkyl.

The term "alkyl" as used herein refers to a monovalent straight- or branched-chain alkyl moiety containing from 1 to 40 carbon atoms. Examples of alkyl groups include alkyl groups containing from 1 to 30 carbon atoms, e.g. from 1 to 20 carbon atoms, e.g. from 1 to 14 carbon atoms. Particular examples include alkyl groups containing 4, 5, 6, 7 or 8 carbon atoms. Unless specifically indicated otherwise, the term "alkyl" does not include optional substituents.

The term "cycloalkyl" as used herein refers to a monovalent saturated aliphatic hydrocarbyl moiety containing from 3 to 40 carbon atoms and containing at least one ring, wherein said ring has at least 3 ring carbon atoms. The cycloalkyl groups mentioned herein may optionally have alkyl groups attached thereto. Examples of cycloalkyl groups include cycloalkyl groups containing from 3 to 16 carbon atoms, e.g. from 3 to 10 carbon atoms. Particular examples include cycloalkyl groups containing 3, 4, 5 or 6 ring carbon atoms. Examples of cycloalkyl groups include groups that are monocyclic, polycyclic (e.g. bicyclic) or bridged ring system. Examples of cycloalkyl groups include cyclopropyl, cyclobutyl, cyclopentyl, cyclohexyl and the like. "Cycloalkenyl" groups correspond to non-aromatic cycloalkyl groups containing at least one carbon-carbon double bond.

The term "alkenyl" as used herein refers to a monovalent straight- or branched-chain alkyl group containing from 2 to 40 carbon atoms and containing, in addition, at least one carbon-carbon double bond, of either E or Z configuration unless specified. Examples of alkenyl groups include alkenyl groups containing from 2 to 28 carbon atoms, e.g. from 3 to 26 carbon atoms, e.g. from 4 to 24 carbon atoms.

The term "aryl" as used herein refers to an aromatic carbocyclic ring system containing from 6 to 14 ring carbon atoms. Examples of aryl groups include aryl groups containing from 6 to 10 ring carbon atoms, e.g. 6 ring carbon atoms. An example of an aryl group includes a group that is a monocyclic aromatic ring system or a polycyclic ring system containing two or more rings, at least one of which is aromatic. Examples of aryl groups include aryl groups that comprise from 1 to 6 exocyclic carbon atoms in addition to ring carbon atoms. Examples of aryl groups include aryl groups that are monovalent or polyvalent as appropriate. Examples of monovalent aryl groups include phenyl, benzyl naphthyl, fluorenyl, azulenyl, indenyl, anthryl and the like. An example of a divalent aryl group is 1,4-phenylene.

The term "alkylene" as used herein refers to a divalent straight- or branched-chain saturated hydrocarbyl group consisting of hydrogen and carbon atoms and containing from 1 to 30 carbon atoms. Examples of alkylene groups include alkylene groups that contain from 1 to 20 carbon atoms, e.g. from 1 to 12 carbon atoms, e.g. from 1 to 10 carbon atoms. Particular examples include alkylene groups that contain 1, 2, 3, 4, 5 or 6 carbon atoms.

The term "cycloalkyl-substituted-alkyl" as used herein refers to a straight- or branched-chain alkyl group in which one of the hydrogens of the alkyl chain is replaced with a cycloalkyl group as described hereinabove.

In some embodiments, the α,β-unsaturated aldehyde employed in the process of the invention has the formula (I):

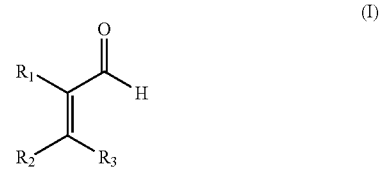

where $R_1$ and $R_3$ are independently selected from H and aliphatic hydrocarbyl; and $R_2$ is aliphatic hydrocarbyl, preferably wherein $R_1$ and $R_2$ are aliphatic hydrocarbyl and $R_3$ is H.

In particularly preferred embodiments, $R_1$ and $R_3$ are independently selected from H, $C_1$-$C_{18}$ alkyl, $C_3$-$C_{18}$ cycloalkyl and $C_4$-$C_{18}$ cycloalkyl-substituted-alkyl and $R_2$ is $C_1$-$C_{18}$ alkyl, $C_3$-$C_{18}$ cycloalkyl and $C_4$-$C_{18}$ cycloalkyl-substituted-alkyl. Preferred examples of the α,β-unsaturated aldehyde for use in the process of the present invention include E/Z-2-decyltetradec-2-enal.

In some embodiments, the trihydrocarbyl orthoester employed in the process of the invention is of formula (II):

where $R_4$ is selected from $C_4$-$C_{40}$ alkyl, $C_3$-$C_{40}$ cycloalkyl and $C_4$-$C_{40}$ cycloalkyl-substituted-alkyl and $R_5$ is selected from H and $C_1$-$C_{12}$ alkyl, $C_3$-$C_{12}$ cycloalkyl and $C_4$-$C_{12}$ cycloalkyl-substituted-alkyl.

In some embodiments, $R_4$ is $C_4$-$C_{40}$ alkyl, preferably $C_4$-$C_{20}$ alkyl, preferably $C_6$-$C_{18}$ alkyl, most preferably $C_8$-$C_{12}$ alkyl.

In some embodiments, $R_5$ is selected from H and $C_1$-$C_{12}$ alkyl, preferably from H and $C_1$-$C_4$ alkyl, most preferably H.

Preferred examples of the trihydrocarbyl orthoesters include tri-2-methylbutyl orthoformate and tri-2-ethylhexyl orthoformate and combinations thereof.

In some embodiments, the ether formed by the process of the invention has a total number of carbon atoms of from 20 to 50, preferably from 22 to 40, more preferably from 24 to 30 carbon atoms, and most preferably from 28 to 30 carbon atoms.

The ether compounds described herein may be used to improve the dispersancy properties (for example, by improving soot and sludge dispersancy) and/or viscosity profile (for example, by decreasing deposit forming tendency and/or reducing oxidatively induced thinkening) of a lubricant composition, such as a lubricant composition for an internal combustion engine, preferably associated with an automotive vehicle.

Ether compounds which may be prepared in accordance with the process of the present invention may be particularly suited for blending into a lubricant composition. In particular, such ether compounds may be miscible with conventional base stocks, including hydrocarbon base stocks, as well as with conventional lubricant additives. Moreover, such ether compounds may be used in a lubricant composition for example, in an amount of greater than about 1% by weight, such as greater than about 5% by weight, greater than about 10% by weight, greater than about 20% by weight or greater than about 30% by weight whilst meeting elastomer compatibility requirements for lubricant compositions.

The process of the present invention may be utilized in order to prepare ether compounds from a wide range of commercially available α,β-unsaturated aldehyde and trihydrocarbyl orthoester feedstocks or reactants readily prepared from such feedstocks.

In some embodiments, the compounds are prepared from bio-derived feedstocks. For instance, the resulting ether compounds may contain greater than about 50%, such as greater than about 70%, or greater than about 80% by weight of biobased carbon. The biobased carbon content of the compounds may be measured according to ASTM D6866.

In accordance with the process of the present invention, the α,β-unsaturated aldehyde and the trihydrocarbyl orthoester reactants are reacted so as to form an α,β-unsaturated acetal. Reaction of the α,β-unsaturated aldehyde and the trihydrocarbyl orthoester is preferably catalyzed by an acid. Examples of acid catalysts that may be used include p-toluenesulfonic acid, benzenesulfonic acid, methanesulfonic acid, sulfuric acid, hydrochloric acid, phosphoric acid and an acidic ion-exchange resin. Most preferably the acid catalyst which is employed is p-toluenesulfonic acid.

Examples of suitable acidic ion-exchange resins include acidic macroreticular-type ion-exchange resin or an acidic gel-type ion-exchange resin. Typically, the acidic gel-type cation exchange resins that may be used are based on an insoluble cross-linked polymeric matrix, typically having a pore diameter of at most 30 Å. In preferred embodiments, the acidic gel-type cation exchange resins are based on a cross-linked polystyrene based matrix, preferably having a pore diameter of at most 30 Å. More preferably, the acidic gel-type cation exchange resins that may be used are based on a cross-linked polymeric matrix prepared by copolymerising styrene and divinyl benzene and preferably having a pore diameter of at most 30 Å.

In preferred embodiments, the acidic gel-type cation exchange resins are strong acid ion exchange resins, such as sulfonated resins. In particular, the acidic gel-type cation exchange resins are preferably based on a sulfonated insoluble cross-linked polymeric matrix preferably having a pore diameter of at most 30 Å. In a particularly preferred embodiment, the acidic gel-type cation exchange resin used is based on a sulfonated copolymer of styrene and divinyl benzene, preferably having a pore diameter of at most 30 Å.

Examples of suitable acidic gel-type cation exchange resins include, but are not limited to, the strong acid Dowex (trademark) gel-type ion exchange resins, the strong acid Amberlyst (trademark) gel-type ion exchange resins, the strong acid Diaion (trademark) gel-type ion exchange resins, the strong acid Lewatit (trademark) gel-type ion exchange resins, the strong acid Purolite (trademark) gel-type ion exchange resins, the strong acid gel-type ion exchange resins available from ResinTech Inc., and mixtures thereof.

The acidic macroreticular-type cation exchange resins useful in the present invention are typically based on an insoluble cross-linked polymeric matrix typically having a pore diameter in the range of from 50 to 1,000,000 Å. In preferred embodiments, the acidic macroreticular-type cation exchange resins used in the process of the present invention are based on a cross-linked polystyrene based matrix having a pore diameter in the range of from 50 to 1,000,000 Å. More preferably, the acidic macroreticular-type cation exchange resins useful in the process of the present invention are based on a cross-linked polymeric matrix prepared by copolymerising styrene and divinyl benzene, having a pore diameter in the range of from 50 to 1,000,000 Å.

In preferred embodiments, the acidic macroreticular-type cation exchange resins used in the process of the present invention are strong acid ion exchange resins, such as sulfonated resins. In particular, the acidic macroreticular-type cation exchange resins used in the process of the present invention are preferably based on a sulfonated insoluble cross-linked polymeric matrix preferably having a pore diameter in the range of from 50 to 1,000,000 Å. Thus, in a particularly preferred embodiment, the acidic macroreticular-type cation exchange resins used in the process of the present invention are sulfonated copolymers of styrene and divinyl benzene, having a pore diameter in the range of from 50 to 1,000,000 Å.

Suitable acidic macroreticular-type cation exchange resins include, but are not limited to, the strong acid Dowex macroreticular-type ion exchange resins, the strong acid Amberlyst macroreticular-type ion exchange resins, the strong acid Diaion macroreticular-type ion exchange resins, the strong acid Lewatit macroreticular-type ion exchange resins, the strong acid Purolite macroreticular-type ion exchange resins, the strong acid macroreticular-type ion exchange resins available from ResinTech Inc., and mixtures thereof.

The α,β-unsaturated aldehyde and the trihydrocarbyl orthoester reactants may be contacted by any suitable means of which the skilled person is familiar. For instance, the reactants may be contacted within a reactor and may be fed into the reactor either separately or pre-mixed. Where an acidic ion-exchange resin is employed as an acidic catalyst, the reactants may initially all contact the solid catalyst at the same portion of the solid catalyst, or they may be added at different positions of the solid catalyst. The initial point of contact of the reactants with the solid catalyst is the point at which the reactants initially contact each other in the presence of the solid catalyst. The reactants may flow co-currently or counter-currently over the solid catalyst.

The process of the present invention may be carried out in any suitable heterogeneous or homogeneous catalytic reactor, in particular the known types of liquid-phase reactors (including but not limited to plug flow, continuously stirred tank, loop reactors or combinations thereof). Reactive separations, such as catalytic distillation, can also be employed in accordance with the present invention, which may be useful in a continuous process where production and removal of products occurs simultaneously. The reactants may be in a gaseous phase and/or a liquid phase. The reaction can be carried out in a continuous, semi-continuous or a batch-type mode.

The α,β-unsaturated aldehyde and the trihydrocarbyl orthoester reactants are contacted at a temperature which is suitable for achieving conversion of a major portion of the aldehyde reactant to the corresponding acetal and which avoids decomposition of the reactants and does not, for instance, exceed the temperature limit at which any solid acidic catalyst which is present remains stable. In particular, where an acidic ion-exchange resin is employed in connection with the invention, high temperatures can lead to resin decomposition and leaching which is undesirable. A suitable range of temperatures for use in connection with the acetalization reaction where an acidic ion-exchange resin catalyst is employed of the present invention is from 30° C. to 120° C. In preferred embodiments, the reactants are contacted at a temperature of from 50° C. to 100° C., more preferably from 70° C. to 90° C., for example 80° C., when an acidic ion-exchange resin catalyst is employed. Higher temperatures may be used where alternative acidic catalysts are used, such as those described hereinbefore. For example, the reaction may be conducted over temperatures from 50° C. to 150° C., preferably from 70° C. to 140° C., more preferably from 80° C. to 120° C.

The reaction of the α,β-unsaturated aldehyde and the trihydrocarbyl orthoester may be performed over a range of pressures. A suitable range of pressures for use in connection with the present invention is from 50 kPa to 5,000 kPa. In preferred embodiments, the reactants are contacted at a pressure from 100 kPa to 1,000 kPa, more preferably from, 100 kPa to 500 kPa, for example from 100 kPa to 250 kPa.

In preferred embodiments, the acetalization reaction between the α,β-unsaturated aldehyde and the trihydrocarbyl orthoester in step i) of the process is performed under an inert atmosphere, preferably under a nitrogen atmosphere.

In preferred embodiments, the α,β-unsaturated aldehyde and the trihydrocarbyl orthoester reactants are contacted in the liquid phase. Optionally, solvents may be used for diluting the reaction mixture, provided they do not negatively impact the acetalization reaction. Suitable solvents include aprotic, hydrocarbon solvents such as pentane, heptane and/or toluene.

Where a bed of solid acid catalyst, i.e. an acidic ion-exchange resin, is employed in connection with the acetalization reaction, the flow rate of reactants, in terms of Liquid Hourly Space Velocity (LHSV) (volume of liquid feed stream/total volume of acetalization catalyst/hour), at which a pre-mixed α,β-unsaturated aldehyde/trihydrocarbyl orthoester reactant stream is contacted with the acidic ion-exchange resin catalyst is suitably in the range of from 0.1 to 50 h$^{-1}$.

Following completion of the acetalization reaction, the acetal intermediate may be isolated from the reaction mixture by known separation processes including filtration, chromatography (e.g. flash column chromatography) and/or distillation (e.g. vacuum distillation). Where a homogeneous acid catalyst is used for catalysing the transesterification reaction, a neutralization step may be included as part of isolating the acetal compound, such as washing with alkaline, for example a saturated aqueous sodium bicarbonate.

The trihydrocarbyl orthoester reactant utilized in the process of the present invention contributes towards the structure of the resulting ether by contributing the —OR group. Common orthoesters that are known from protecting group chemistry include trimethyl orthoformate and triethyl orthoformate. These compounds are capable of adding two —OMe or two —OEt groups to the aldehyde carbonyl group, respectively, so as to form the corresponding acetal, as illustrated in Scheme I below. Subsequent loss of one of these —OR groups in the acetal gives rise to the desired ether formation.

Scheme I

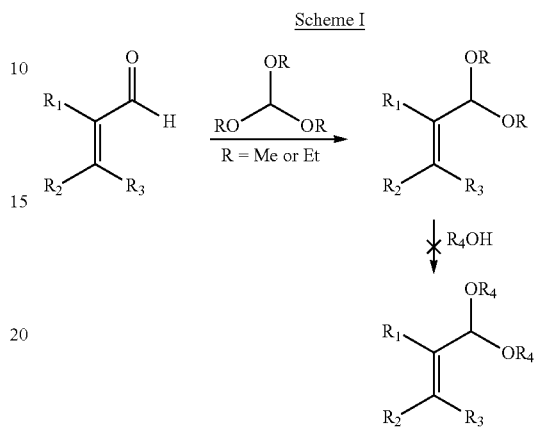

In order to build more complex ether derivatives, investigations were completed by the inventors to determine the most expedient route towards the formation of the desired ether. Investigations included the use of trimethyl orthoformate/triethyl orthoformate in the acetalization of the α,β-unsaturated aldehydes, followed by a transacetalization reaction with an alcohol in an attempt to introduce more complex, longer-chained hydrocarbyl groups. However, such transacetalization reactions on the acetal intermediate were found to be unsuccessful (as shown in Scheme I above).

An alternative approach utilized successfully by the inventors has been found instead to involve transesterifying, for instance, trimethyl orthoformate/triethyl orthoformate with an alcohol, for instance having a long-chained hydrocarbyl portion, in the presence of an acidic catalyst. This approach has been found to be a reliable and convenient means for generating more complex orthoesters which may subsequently be used in the acetalization reaction described above, from which particularly desirable ethers may be formed.

Therefore, in some embodiments, the process of the invention may further comprise a preceding step of preparing the trihydrocarbyl orthoester reactant for use in the acetalization reaction. For example, the process may further comprise the preceding step of preparing a trihydrocabyl orthoester of formula (II) by reacting a trimethyl orthoester and/or triethyl orthoester with a molar excess of an alcohol of formula R$_4$OH in the presence of an acidic catalyst, where R$_4$ is C$_4$-C$_{40}$ alkyl, C$_3$-C$_{40}$ cycloalkyl and C$_4$-C$_{40}$ cycloalkyl-substituted-alkyl, as illustrated in Scheme II below.

Scheme II

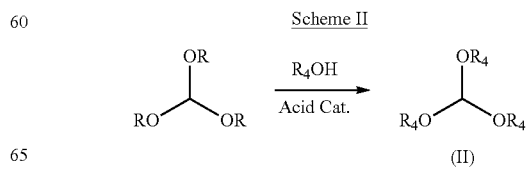

Suitable temperatures and pressures over which the transesterification reaction may be conducted are the same as those for the subsequent acetalization reaction described above. In order to promote the transesterification reaction of trimethyl orthoformate/triethyl orthoformate, a significant molar excess of an alcohol is preferably used relative to the orthoester. In preferred embodiments, the alcohol of formula R₄OH and the orthoester are contacted in a molar ratio is of at least 5:1, more preferably at least 8:1, most preferably at least 10:1.

The acidic catalysts described hereinbefore in connection with the acetalization reaction may also be used for catalyzing a preceding transesterification reaction. Thus, the acidic catalyst may, for example, be selected from p-toluenesulfonic acid, benzenesulfonic acid, methanesulfonic acid, sulfuric acid, hydrochloric acid, phosphoric acid and an acidic ion-exchange resin. Preferably the acid catalyst employed for the transesterification is p-toluenesulfonic acid.

Following completion of a preceding transesterification reaction, the transesterified orthoester may be isolated from the reaction mixture by known separation processes including filtration, chromatography (e.g. flash column chromatography) and/or distillation (e.g. vacuum distillation). Where a homogeneous acid catalyst is used for catalysing the transesterification reaction, (i.e. those acidic catalysts described above other than the acidic ion exchange resin) it is preferred that the same acid catalyst is subsequently employed in the acetalization reaction since it makes purification of the transesterified orthoester less onerous and obviates the requirement for removing substantially all the catalyst prior to the acetalization reaction.

Once the transesterified orthoester has been obtained, this may be used in the acetalization reaction as described hereinbefore and as illustrated in Scheme III below.

Scheme III

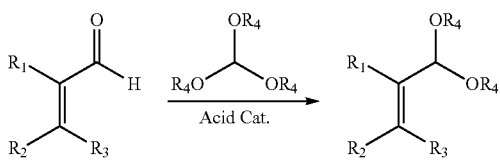

Following acetalization, the acetal is converted to the ether by means of hydrogenolysis in accordance with the process of the present invention. Advantageously, hydrogenolysis of the acetal may be accompanied by hydrogenation of the double bond deriving from the α,β-unsaturated aldehyde in the same step (i.e. a one-pot hydrogenolysis and hydrogenation reaction), thereby minimizing the number of process steps, as illustrated in Scheme IV below.

Scheme IV

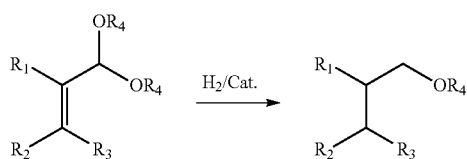

The unsaturated acetal compound is converted to the saturated ether typically by catalytic hydrogenolysis/hydrogenation in the presence of a supported hydrogenation catalyst. A further advantage of performing a hydrogenation with the acetal, as opposed to hydrogenation of the α,β-unsaturated aldehyde, is that a broader range of hydrogenation conditions and catalysts may also be relied upon in comparison to the restricted conditions and catalyst options available where a selective hydrogenation is undertaken. More specifically, hydrogenation of an α,β-unsaturated aldehyde prior to acetalization requires that hydrogenation conditions are selective for hydrogenation at the double bond of the α,β-unsaturated aldehyde, as opposed to the carbonyl group of that compound. Moreover, hydrogenation of acetals requires forcing conditions and therefore there is little risk of acetal hydrogenation accompanying hydrogenation at the carbon-carbon double bond under desirable and economical hydrogenation conditions.

The hydrogenolysis/hydrogenation reaction may be performed at any suitable pressures and temperatures at which the saturated ether is formed at an acceptable reaction rate, without risk of decomposition or substantial by-product formation that would otherwise negatively impact upon the advantages of the invention. Hydrogenolysis/hydrogentation is, for example, suitably carried out at pressures of from 1,500 kPa absolute to 30,000 kPa absolute, preferably from 5,000 kPa absolute to 15,000 kPa absolute, more preferably from 7,500 kPa absolute to 12,500 kPa absolute. Suitable temperatures at which the hydrogenolysis/hydrogenation may be performed are, for example, from 100° C. to 350° C., preferably from 125° C. to 300° C., more preferably from 150° C. to 270° C. The molar ratio of the acetal to hydrogen can be from about 1:2 to about 1:100, and is preferably from about 1:4 to about 1:50.

Where a bed of hydrogenation catalyst is employed in connection with the hydrogenation/hydrogenolysis reaction, the flow rate of hydrogen-containing gas stream, in terms of Gas Hourly Space Velocity (GHSV) (volume of hydrogen-containing feed stream/total volume of hydrogenation catalyst/hour), at which acetal reactant is contacted with hydrogen, or a mixture of hydrogen with inert gases, is suitably in the range of from 50 to 10,000 $h^{-1}$.

Where a bed of hydrogenation catalyst is employed in connection with the hydrogenation/hydrogenolysis reaction, the flow rate of a α,β-unsaturated acetal feed stream, in terms of Liquid Hourly Space Velocity (LHSV) (volume of feed stream/total volume of hydrogenation catalyst/hour), over the catalyst bed, is suitably in the range of from 5 to 1,000 $h^{-1}$, preferably from 10 to 500 $h^{-1}$, more preferably from 20 to 200 $h^{-1}$, most preferably from 25 to 100 $h^{-1}$.

In some embodiments, the hydrogenation catalyst useful in the hydrogenation/hydrogenolysis reaction comprises a metal selected from nickel, palladium, platinum, rhodium, ruthenium, cobalt, copper and combinations thereof. Preferably, the catalyst comprises palladium. The catalyst may be supported with a support material selected from carbon, silica, alumina, silica-alumina, and aluminosilicate, preferably carbon. The carbon, where used, can be any one of the many forms of carbon e.g. graphite or activated carbon.

The catalytic metal may be deposited or impregnated on the support using conventional mixing or precipitation techniques. The catalyst composition suitably has a catalytic metal content of about 0.05% w/w to about 80% w/w. Within this range, when a relatively less active metal, such as nickel, is used as the catalytic metal, it is suitably used towards the higher end of this range, whereas when a relatively more active metal such as palladium is used as the catalytic metal, it is preferably used at the lower end of this range. The skilled person is able to select a suitable metal loading depending on the particular catalytic metal used. Thus, for instance, the preferred range for the less active catalytic metals is suitably from about 20% w/w to about 80% w/w, whereas for the more active catalytic metals, such as palladium, the preferred range is from about 0.05% w/w to about 20% w/w. These weight ranges are based solely on the weight of the catalytic metal and the support and does not take into account any water or moisture content associated with either component.

The hydrogenation/hydrogenolysis reaction may optionally be carried out in the presence of a solvent. Examples of such solvents include aprotic, hydrocarbon solvents such as pentane, heptane and/or toluene. A sufficient amount of solvent can be used to dilute the acetal reactant to the desired concentration to facilitate handling and/or to maintain the reaction mass in solution.

The hydrogenation/hydrogenolysis of the acetal with hydrogen in the presence of a catalyst composition as described above can be carried out in a slurry reactor, a fixed bed reactor, a spouted bed reactor or any other suitable reactor configuration such as, for example, a moving bed reactor. The acetal reactant may be in a gaseous phase and/or a liquid phase. The reaction can be carried out in a continuous, semi-continuous or a batch-type mode. The average residence time of the acetal reactant in contact with the catalyst composition during the formation of the corresponding saturated ether compound is suitably from about 5 minutes to about 30 hours, preferably from about 15 minutes to about 10 hours.

The desired ether product may be isolated from the reaction mixture, in particular the alcohol by-product of the hydrogenolysis reaction deriving from the acetal group, by known separation processes including filtration, chromatography (e.g. flash column chromatography) and/or distillation (e.g. vacuum distillation), filtration and distillation being favoured on an industrial scale.

A particular benefit of the present invention is that the advantages of using an α,β-unsaturated aldehyde as a starting material, particularly in terms of the structural properties of the resulting ether derived therefrom, may be capitalized upon in a manner which maximizes selectivity as well as process economy. By introducing desired functionality intended for the end product ether into an trihydrocarbyl orthoester reactant, as opposed to an alternative reactant such as an alcohol, high selectivity can be achieved in terms of yield of the desired ether, and without the formation of corrosive intermediates that can be problematic in prior art processes. Moreover, achieving hydrogenation of the double bond and hydrogenolysis of the acetal group to provide a saturated ether in one step is particularly advantageous over an alternative route to ether preparation where those reactions are performed separately. The present invention obviates the requirement for a selective hydrogenation of the double bond of the α,β-unsaturated aldehyde starting material that would otherwise be necessary and which can be detrimental to overall product yield. Moreover, hydrogenation of α,β-unsaturated aldehydes to provide the saturated aldehyde derivative must proceed selectively so as to avoid hydrogenation at the carbonyl group, thereby significantly restricting the reaction conditions and catalysts that may be used. By instead undertaking hydrogenation at a later stage in the synthesis and with an acetal compound as opposed to an aldehyde, the reaction conditions and catalysts that may be used may be selected without concern over the selectivity of the hydrogenation, thus allowing more economically favourable conditions to prevail.

In some embodiments, the process of the present invention may further include the step of blending the ether product obtained from the process into a lubricant composition.

The process of the present invention therefore represents a means of preparing an ether which is useful as a lubricating base stock which avoids the formation of corrosive intermediates and which may be isolated from the reaction mixture more readily. By operating the etherification process in accordance with the present invention, it is possible to provide good conversion of the aldehyde to the ether product, and with high selectivity.

In accordance with another embodiment, the process of the invention also further comprises blending the ether obtained from the process into a lubricant composition by blending the ether with one or more additional base stocks and/or one or more lubricant additives. The ether obtained from the process of the invention may be miscible with conventional base stocks, including hydrocarbon base stocks, as well as with conventional lubricant additives. Moreover, such ether compounds may be used in a lubricant composition for example, in an amount of greater than about 1% by weight, such as greater than about 5% by weight, greater than about 10% by weight, greater than about 20% by weight or greater than about 30% by weight.

Base stocks other than the ether compound formed in the process of the present invention which are suitable for use blending for preparing a lubricant composition include non-aqueous base stocks, such as Group I, Group II, Group III, Group IV and Group V base stocks.

The lubricant composition may comprise a single lubricant additive, though it will typically comprise a combination of lubricant additives. The lubricant additives will typically be present in the lubricant composition in an amount of from about 5% to about 40% by weight, such as about 10% to about 30% by weight.

Suitable lubricant additives include detergents (including metallic and non-metallic detergents), friction modifiers, dispersants (including metallic and non-metallic dispersants), viscosity modifiers, dispersant viscosity modifiers, viscosity index improvers, pour point depressants, anti-wear additives, rust inhibitors, corrosion inhibitors, antioxidants (sometimes also called oxidation inhibitors), anti-foams (sometimes also called anti-foaming agents), seal swell agents (sometimes also called seal compatibility agents), extreme pressure additives (including metallic, non-metallic, phosphorus containing, non-phosphorus containing, sulphur containing and non-sulphur containing extreme pressure additives), surfactants, demulsifiers, anti-seizure agents, wax modifiers, lubricity agents, anti-staining agents, chromophoric agents, metal deactivators, and mixtures of two or more thereof.

In some embodiments, the lubricant composition comprises a detergent. Examples of detergents include ashless detergents (that is, non-metal containing detergents) and metal-containing detergents. Suitable non-metallic detergents are described for example in U.S. Pat. No. 7,622,431. Metal-containing detergents comprise at least one metal salt of at least one organic acid, which is called soap or surfactant. Suitable organic acids include for example, sulphonic acids, phenols (suitably sulphurised and including for example, phenols with more than one hydroxyl group, phenols with fused aromatic rings, phenols which have been modified for example, alkylene bridged phenols, and Mannich base-condensed phenols and saligenin-type phenols, produced for example by reaction of phenol and an aldehyde under basic conditions) and sulphurised derivatives thereof, and carboxylic acids including for example, aromatic carboxylic acids (for example hydrocarbyl-substituted salicylic acids and derivatives thereof, for example hydrocarbyl substituted salicylic acids and sulphurised derivatives thereof).

In some embodiments, the lubricant composition comprises a friction modifier. Suitable friction modifiers include for example, ash-producing additives and ashless additives. Examples of suitable friction modifiers include fatty acid derivatives including for example, fatty acid esters, amides, amines, and ethoxylated amines. Examples of suitable ester friction modifiers include esters of glycerol for example, mono-, di-, and tri-oleates, mono-palmitates and mono-myristates. A particularly suitable fatty acid ester friction modifier is glycerol monooleate. Examples of suitable friction modifiers also include molybdenum compounds for example, organo molybdenum compounds, molybdenum dialkyldithiocarbamates, molybdenum dialkylthiophosphates, molybdenum disulphide, tri-molybdenum cluster dialkyldithiocarbamates, non-sulphur molybdenum compounds and the like. Suitable molybdenum-containing compounds are described for example, in EP 1533362 A1 for example in paragraphs [0101] to [0117].

In some embodiments, the lubricant composition comprises a dispersant. Examples of suitable ashless dispersants include oil soluble salts, esters, amino-esters, amides, imides and oxazolines of long chain hydrocarbon-substituted mono- and polycarboxylic acids or anhydrides thereof; thiocarboxylate derivatives of long chain hydrocarbons; long chain aliphatic hydrocarbons containing polyamine moieties attached directly thereto; Mannich condensation products formed by condensing a long chain substituted phenol with formaldehyde and polyalkylene polyamine; Koch reaction products and the like.

In some embodiments, the lubricant composition comprises a dispersant viscosity modifier. Examples of suitable dispersant viscosity modifiers and methods of making them are described in WO 1999/021902, WO 2003/099890 and WO 2006/099250.

In some embodiments, the lubricant composition comprises a viscosity index improver. Examples of suitable viscosity modifiers include high molecular weight hydrocarbon polymers (for example polyisobutylene, copolymers of ethylene and propylene and higher alpha-olefins); polyesters (for example polymethacrylates); hydrogenated poly (styrene-co-butadiene or isoprene) polymers and modifications (for example star polymers); and esterified poly (styrene-co-maleic anhydride) polymers. Oil-soluble viscosity modifying polymers generally exhibit number average molecular weights of at least about 15000 to about 1000000, such as about 20000 to about 600000 as determined by gel permeation chromatography or light scattering methods.

In some embodiments, the lubricant composition comprises a pour point depressant. Examples of suitable pour point depressants include $C_8$ to $C_{18}$ dialkyl fumarate/vinyl acetate copolymers, methacrylates, polyacrylates, polyarylamides, polymethacrylates, polyalkyl methacrylates, vinyl fumarates, styrene esters, condensation products of haloparaffin waxes and aromatic compounds, vinyl carboxylate polymers, terpolymers of dialkyfumarates, vinyl esters of fatty acids and allyl vinyl ethers, wax naphthalene and the like. In at least some examples, the at least one lubricant additive includes at least one anti-wear additive. Examples of suitable anti-wear additives include non-phosphorus containing additives for example, sulphurised olefins. Examples of suitable anti-wear additives also include phosphorus-containing anti-wear additives. Examples of suitable ashless phosphorus-containing anti-wear additives include trilauryl phosphite and triphenylphosphorothionate and those disclosed in paragraph [0036] of US 2005/0198894. Examples of suitable ash-forming, phosphorus-containing anti-wear additives include dihydrocarbyl dithiophosphate metal salts. Examples of suitable metals of the dihydrocarbyl dithiophosphate metal salts include alkali and alkaline earth metals, aluminium, lead, tin, molybdenum, manganese, nickel, copper and zinc. Particularly suitable dihydrocarbyl dithiophosphate metal salts are zinc dihydrocarbyl dithiophosphates (ZDDP).

In some embodiments, the lubricant composition comprises a rust inhibitor. Examples of suitable rust inhibitors include non-ionic polyoxyalkylene polyols and esters thereof, polyoxyalkylene phenols, polyoxyalkylene polyols, anionic alky sulphonic acids, zinc dithiophosphates, metal phenolates, basic metal sulphonates, fatty acids and amines.

In some embodiments, the lubricant composition comprises a corrosion inhibitor. Examples of suitable corrosion inhibitors include phosphosulphurised hydrocarbons and the products obtained by the reaction of phosphosulphurised hydrocarbon with an alkaline earth metal oxide or hydroxide, non-ionic polyoxyalkylene polyols and esters thereof, polyoxyalkylene phenols, thiadiazoles, triazoles and anionic alkyl sulphonic acids. Examples of suitable epoxidised ester corrosion inhibitors are described in US 2006/0090393.

In some embodiments, the lubricant composition comprises an antioxidant. Examples of suitable antioxidants include alkylated diphenylamines, N-alkylated phenylenediamines, phenyl-a-naphthylamine, alkylated phenyl-a-naphthylamines, dimethylquinolines, trimethyldihydroquinolines and oligomeric compositions derived therefrom, hindered phenolics (including ashless (metal-free) phenolic compounds and neutral and basic metal salts of certain phenolic compounds), aromatic amines (including alkylated and non-alkylated aromatic amines), sulphurised alkyl phenols and alkali and alkaline earth metal salts thereof, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds (for example, copper dihydrocarbyl thio- or thio-phosphate, copper salts of a synthetic or natural carboxylic acids, for example a $C_8$ to $C_{18}$ fatty acid, an unsaturated acid or a branched carboxylic acid, for example basic, neutral or acidic Cu(I) and/or Cu(II) salts derived from alkenyl succinic acids or anhydrides), alkaline earth metal salts of alkylphenolthioesters, suitably containing $C_5$ to $C_{12}$ alkyl side chains, calcium nonylphenol sulphide, barium t-octylphenyl sulphide, dioctylphenylamine, phosphosulphised or sulphurised hydrocarbons, oil soluble phenates, oil soluble sulphurised phenates, calcium dodecylphenol sulphide, phosphosulphurised hydrocarbons, sulphurised hydrocarbons, phosphorus esters, low sulphur peroxide decomposers and the like.

In some embodiments, the lubricant composition comprises an antifoam agent. Examples of suitable anti-foam agents include silicones, organic polymers, siloxanes (including poly siloxanes and (poly) dimethyl siloxanes, phenyl methyl siloxanes), acrylates and the like.

In some embodiments, the lubricant composition comprises a seal swell agent. Examples of suitable seal swell agents include long chain organic acids, organic phosphates, aromatic esters, aromatic hydrocarbons, esters (for example butylbenzyl phthalate) and polybutenyl succinic anhydride.

The lubricant composition may comprise lubricant additives in the amounts shown in Table 2.

TABLE 2

| Additive type | Lubricant composition | |
|---|---|---|
| | Suitable amount (actives) if present by weight | Preferred amount (actives) if present by weight |
| Phosphorus-containing anti-wear additives | Corresponding to about 10 to about 6000 ppm P | Corresponding to about 10 to about 1000 ppm P |
| Molybdenum-containing anti-wear additives | Corresponding to about 10 to about 1000 ppm Mo | Corresponding to about 40 to about 600 ppm Mo |
| Boron-containing anti-wear additives | Corresponding to about 10 to about 500 ppm B | Corresponding to about 50 to about 100 ppm B |
| Friction modifiers | About 0.01 to about 5% | About 0.01 to about 1.5% |
| Molybdenum-containing friction modifiers | Corresponding to about 10 to about 1000 ppm Mo | Corresponding to about 400 to about 850 ppm Mo |
| Dispersants | About 0.1 to about 20% | About 0.1 to about 8% |
| Detergents | About 0.01 to about 6% | About 0.01 to about 4% |
| Viscosity index improvers | About 0.01 to about 20% | About 0.01 to about 15% |
| Pour point depressants | About 0.01 to about 5% | About 0.01 to about 1.5% |
| Corrosion and/or rust inhibitors | About 0.01 to about 5% | About 0.01 to about 1.5% |
| Anti-oxidants | About 0.01 to about 10% | About 0.5 to 5 about % |
| Antifoams containing silicon | Corresponding to about 1 to about 20 ppm Si | Corresponding to about 1 to about 10 ppm Si |

The lubricant compositions preparable in accordance with the present invention may have a kinematic viscosity at 40° C. of less than about 60 cSt, such as less than about 55 cSt, or less than about 50 cSt. The lubricant compositions may have a kinematic viscosity at 100° C. of less than about 12 cSt, such as less than about 10 cSt, or less than about 9.5 cSt. The lubricant compositions may have a viscosity index of greater than about 100, such as greater than about 110, or greater than about 120. The kinematic viscosity at 40° C. and the kinematic viscosity at 100° C. may be measured according to ASTM D445. The viscosity index may be calculated according to ASTM D2270.

The lubricant compositions may have a Noack volatility of less than about 25%, such as less than about 15%, or less than about 10% by weight. Noack volatility may be measured according to CEC-L-40-A-93.

The lubricant compositions may have a viscosity at 150° C. and a shear rate of $10^6$ $s^{-1}$ of no greater than 3 cP, such as no greater than 2.8 cP. This high temperature high shear viscosity may be measured according to CEC-L-36-A-90.

The lubricant compositions may have at least one of:
an oxidative stability performance on a CEC-L-088-02 test indicated by an absolute viscosity increase at 40° C. of no more than 45 cSt, such as no more than 35 cSt or no more than 25 cSt; a fuel economy performance on a CEC-L-054-96 test of at least 2.5%, such as at least 3%; and a piston cleanliness performance on a CEC-L-088-02 test indicated by an overall piston merit of at least 8.5, such as 9.

The lubricant compositions may have a cold-crankcase simulator performance at −30° C. of less than about 3000, such as less than about 2800, or less than about 2750, for example as measured according to ASTM D5293.

Preferred lubricant compositions meet the requirements set out in SAE J300.

In a yet further embodiment of the invention, after the lubricant composition has been prepared, the process may further comprise lubricating a surface with the lubricant composition by supplying the lubricant composition to a surface for lubrication.

Suitable surfaces include those in power transmission systems for example drive lines and gear boxes for example for vehicles including for example passenger vehicles and heavy duty vehicles; and those in internal combustion engines, for example the crankcases of internal combustion engines. Suitable surfaces also include those in turbine bearings for example in water turbine bearings.

Suitable internal combustion engines include, for example, engines used in automotive applications, engines used in marine applications and engines used in land-based power generation plants. The lubricant compositions are particularly suited to use in an automotive internal combustion engine.

The invention will now be described with reference to the accompanying examples, which are not limiting in nature.

EXAMPLES

Example 1—Synthesis of tri-2-ethylhexyl orthoformate [1]

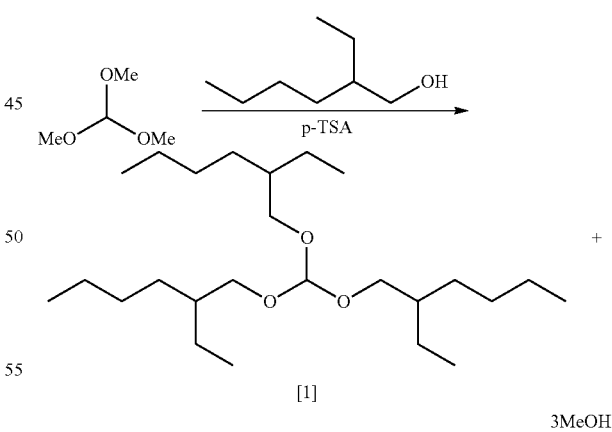

A solution of trimethyl-orthoformate (10 g, 94 mmol) and 2-ethylhexanol (61 g, 470 mmol, 5 equivalents) in a 2-necked round-bottomed flask fitted with a distillation head and a condenser, was treated with p-TSA (1.8 g, 9.4 mmol) and stirred at 60° C. for 10 minutes. After this time the temperature of the reaction was increased (as to maintain a steady take-off of methanol over-head—measuring between 60 to 65° C. at the distillation head) up to a maximum internal reaction temperature of 150° C. Reaction progress was followed by measuring the volume of methanol distillate collected (theoretical yield of methanol is 11.4 mL, 282 mmol). Reaction duration was around 4 h. Once complete the crude reaction mixture was purified by vacuum distillation (without neutralising the p-TSA) to afford the tri-2-ethylhexyl-orthoformate [1] (31.1 g, 75 mmol, 80% yield).

Example 2—Synthesis of tri-2-methylbutyl orthoformate [2]

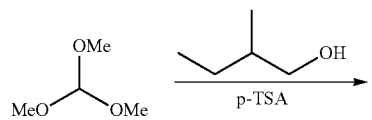

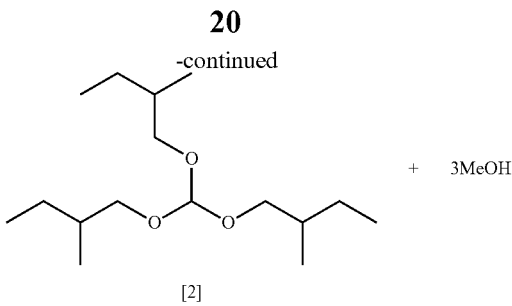

Reaction performed as in Example 1 using 2-methylbutanol as the alcohol source to afford tri-2-methylbutyl orthoformate [2] (90% yield).

Example 3—Synthesis of E/Z-11-(bis((2-methylbutyl)oxy)methyl)tricos-11-ene [3]

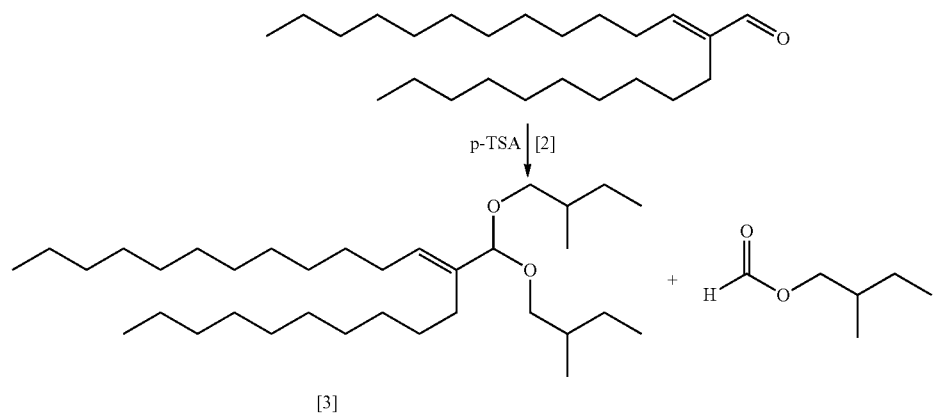

A mixture of tri-2-methylbutyl orthoformate [2] (15 g, 54.7 mmol) and 2-decyltetradec-2-enal (19.2 g, 54.7 mol) was treated with p-TSA (100 mg) and stirred at 80 to 120° C. for 4 h under an atmosphere of $N_2$. Next the reaction mixture was washed with saturated aqueous sodium bicarbonate (50 mL), dried over $MgSO_4$ and concentrated in vacuo to yield the α, β-unsaturated acetal [3] (22 g, 43.3 mmol, 79% yield) and by-product 2-methylbutyl formate.

Example 4—Synthesis of E/Z-11-(bis((2-ethylhexyl)oxy)methyl)tricos-11-ene (41

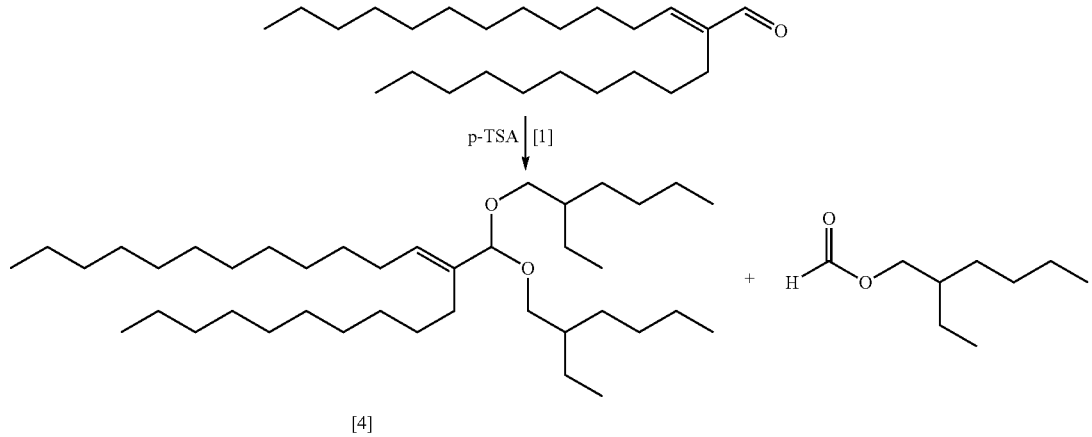

A mixture of tri-2-ethylhexyl orthoformate [1] (20 g, 48.3 mmol) and 2-decyltetradec-2-enal (16.9 g, 48.3 mol) was treated with p-TSA (100 mg) and stirred at 80 to 120° C. for 4 h under an atmosphere of $N_2$. Next the reaction mixture was washed with saturated aqueous sodium bicarbonate (50 mL), dried over $MgSO_4$ and concentrated in vacuo to yield the α, β-unsaturated acetal [4] (25.8 g, 43.4 mmol, 90% yield) and by-product 2-ethylhexyl formate.

Example 5—Synthesis of
11-(((2-ethylhexyl)oxy)methyl)tricosane [5]

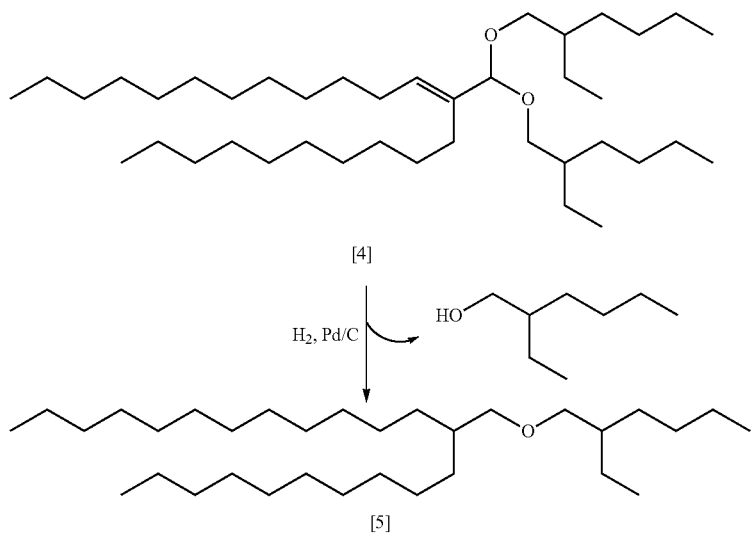

A solution of the α, β-unsaturated acetal [4] (5 g, 0.008 mol) in toluene (100 mL) was hydrogenated at a temperature of 135° C. and a pressure of 100 bar over palladium on charcoal (10 wt. % loading of palladium) to give the crude ether as a 1:1 molar mixture with 2-ethylhexanol in toluene. Next the crude ether was concentrated in vacuo, to remove residual toluene solvent and purified on silica using n-heptane as an eluent to provide the ether 11-(((2-ethylhexyl)oxy)methyl)tricosane [5] (3.2 g, 0.007 mmol, 81% yield) as a colourless oil.

Examples 1-5 demonstrate the high yield and selectivity toward the synthesis of unsymmetrical ethers without employing corrosive halogenated or sulfonate ester intermediates.

Example 6—Assessing Properties of Ether Base Stocks

The following properties of the ether base stock prepared in Example 5, namely 11-(((2-ethylhexyl)oxy)methyl)tricosane [5], were tested:

Kinematic viscosity at 100° C. (KV100) and kinematic viscosity at 40° C. (KV40) were tested according to ASTM D7279.

Viscosity index (VI) was calculated according to ASTM D2270.

Pour point was determined according to ASTM D7346.

Differential scanning calorimetry (DSC) oxidation onset temperature was tested using a method which was based on ASTM E2009 (method B). According to the method, the base stocks were heated from 50° C. to 300° C., at a rate of 50° C./minute, under a pressure of 500 psi in an aluminium SFI pan. The temperature at which an exotherm was observed was recorded.

Noack volatility was measured for 11-(((2-ethylhexyl)oxy)methyl)tricosane [5] in accordance with CEC-L-40-A-93.

The results of the tests are summarized in Table 3, together with results obtained from conventional base stocks (Durasyn 162, a group IV base stock; Durasyn 164, a group IV base stock; Yubase 3, a group II base stock; Yubase 4, a group III base stock; Yubase 4 Plus, a group III base stock; Nexbase 3020, a group II base stock; Nexbase 3030, a group II base stock; Nexbase 3043, a group III base stock; and Chevron 100RLV, a group II base stock).

TABLE 3

| | KV100 (cSt) | KV40 (cSt) | VI | Pour Point (° C.) | DSC Oxidation Onset T (° C.) | Noack (% by weight) |
|---|---|---|---|---|---|---|
| 11-(((2-ethyl-hexyl)oxy)meth-yl)tricosane [5] | 3.5 | 13.7 | 145 | −36 | 205.74 | 5.1 |
| Durasyn 162 | 1.7 | 5.2 | 92 | −72 | 223.61 | THM |
| Durasyn 164 | 4.0 | 17.8 | 126 | −75 | 221.31 | 13.1 |
| Yubase 3 | 3.0 | 14.1 | 105 | −36 | 220.74 | 40.5 |
| Yubase 4 | 4.2 | 19.2 | 126 | −12 | 220.00 | 14.1 |
| Yubase 4 Plus | 4.2 | 18.4 | 138 | −18 | 220.32 | 12.9 |
| Nexbase 3020 | 2.2 | 7.6 | 93 | −51 | 221.66 | THM |
| Nexbase 3030 | 3.0 | 12.0 | 101 | −39 | 221.05 | 38.1 |
| Nexbase 3043 | 4.3 | 19.9 | 124 | −18 | 222.09 | 14.0 |
| Chevron 110RLV | 4.6 | 22.6 | 119 | −15 | 225.86 | 14.6 |

THM = Too high to measure

The results of the tests shown in Table 3 demonstrate that the properties of ether base stocks obtainable by the process of the present invention compare favourably with those of conventional base stocks. The ether base stocks obtainable by the process of the present invention may thus be formulated into a lubricant composition for use in lubrication applications.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope and spirit of this invention.

The invention claimed is:

1. A process for preparing an ether, said process comprising the steps of:

i) contacting an α,β-unsaturated aldehyde of formula (I):

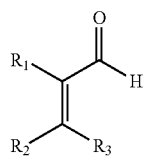

(I)

where $R_1$ and $R_3$ are independently selected from H and aliphatic hydrocarbyl;
and $R_2$ is aliphatic hydrocarbyl,
with a trihydrocarbyl orthoester to form an α,β-unsaturated acetal; and ii) subjecting the α,β-unsaturated acetal obtained from step i) to hydrogenation and hydrogenolysis to hydrogenate at the α- and β-positions of the α,β-unsaturated acetal and to convert the acetal group to an ether.

2. The process of claim 1, wherein $R_1$ and $R_3$ are independently selected from H, $C_1$-$C_{18}$ alkyl, $C_3$-$C_{18}$ cycloalkyl and $C_4$-$C_{18}$ cycloalkyl-substituted-alkyl; and $R_2$ is selected from $C_1$-$C_{18}$ alkyl, $C_3$-$C_{18}$ cycloalkyl and $C_4$-$C_{18}$ cycloalkyl-substituted-alkyl.

3. The process of claim 1, wherein the trihydrocarbyl orthoester is of formula (II):

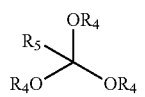

(II)

where $R_4$ is selected from $C_4$-$C_{40}$ alkyl, $C_3$-$C_{40}$ cycloalkyl and $C_4$-$C_{40}$ cycloalkyl-substituted-alkyl and $R_5$ is selected from H and $C_1$-$C_{12}$ alkyl, $C_3$-$C_{12}$ cycloalkyl and $C_4$-$C_{12}$ cycloalkyl-substituted-alkyl.

4. The process of claim 3, further comprising the preceding step of preparing a trihydrocabyl orthoester of formula (II) by reacting a trimethyl orthoester and/or triethyl orthoester with a molar excess of an alcohol of formula $R_4OH$ in the presence of an acidic catalyst, where $R_4$ is $C_4$-$C_{40}$ alkyl, $C_3$-$C_{40}$ cycloalkyl and $C_4$-$C_{40}$ cycloalkyl-substituted-alkyl.

5. The process of claim 4, wherein the alcohol of formula $R_4OH$ and the trimethyl orthoester and/or triethyl orthoester are contacted in a molar ratio of at least 5:1.

6. The process of claim 4, wherein the acidic catalyst is selected from sulfuric acid, p-toluenesulfonic acid, benzenesulfonic acid, hydrochloric acid, phosphoric acid and an acidic ion-exchange resin.

7. The process of claim 1 wherein step i) is conducted in the presence of an acidic catalyst selected from p-toluenesulfonic acid, benzenesulfonic acid, methanesulfonic acid, sulfuric acid, hydrochloric acid, phosphoric acid, and an acidic ion-exchange resin.

8. The process of claim 7, wherein the acidic ion-exchange resin is an acidic macroreticular-type ion-exchange resin or an acidic gel-type ion-exchange resin.

9. The process of claim 1, further comprising the preceding step of preparing the α,β-unsaturated aldehyde of formula (I) by an aldol condensation reaction.

10. The process of claim 1, wherein the α,β-unsaturated aldehyde is contacted with the trihydrocarbyl orthoester in step i) at a temperature in the range of from 50° C. to 150° C.

11. The process of claim 1, wherein hydrogenation and hydrogenolyis in step ii) is performed in the presence of a hydrogenation catalyst, and optionally as a one pot reaction.

12. The process of claim 11, wherein the catalyst comprises a metal selected from nickel, palladium, platinum, rhodium, ruthenium, cobalt, copper and combinations thereof.

13. The process of claim 11, wherein the catalyst is supported with a support material selected from carbon, silica, alumina, silica-alumina, and aluminosilicate.

14. The process of claim 1, wherein hydrogenation and hydrogenolysis in step ii) is conducted at a temperature in the range of from 100° C. to 350° C.

15. The process of claim 1, wherein hydrogenation and hydrogenolysis in step ii) is conducted at a pressure of from 1,500 kPa absolute to 30,000 kPa absolute.

16. The process of claim 1, wherein the ether formed in the process has a total number of carbon atoms of from 20 to 50.

17. The process of claim 1, further comprising blending the ether obtained from the process with one or more additional base stocks and/or one or more lubricant additives into a lubricant composition.

18. The process of claim 17, wherein the ether is present in the lubricant composition in an amount of greater than 1% by weight.

19. The process of claim 17, further comprising supplying the lubricant composition to a surface for lubrication.

20. The process of claim 17, further comprising supplying the lubricant composition to a surface in an internal combustion engine.

* * * * *